US005474561A

United States Patent [19]

Yao

[11] Patent Number: 5,474,561

[45] Date of Patent: Dec. 12, 1995

[54] ALL POSITIONAL AND UNIVERSAL GUIDING DEVICE FOR INTERLOCKING INTRAMEDULLARY NAIL

[76] Inventor: Meei-Huei Yao, 62, Yung-Luh Rd., Ho-Mei Township, Chang-Hua County, Taiwan

[21] Appl. No.: 189,673

[22] Filed: Feb. 1, 1994

[51] Int. Cl.$^6$ .................................................. A61B 17/56

[52] U.S. Cl. .................................................. 606/98

[58] Field of Search .................................. 606/98, 96, 86, 606/102, 103

[56] References Cited

U.S. PATENT DOCUMENTS 5,234,434 8/1993 Goble et al. .............................. 606/98

FOREIGN PATENT DOCUMENTS 3245680 10/1983 Germany .............................. 606/98

221356 4/1985 Germany .............................. 606/98

992045 2/1983 U.S.S.R. .............................. 606/98

*Primary Examiner*—Tamara L. Graysay

*Attorney, Agent, or Firm*—Larson and Taylor

[57] ABSTRACT

An all positional and universal guiding device for interlocking intramedullary nail is provided with a locating seat which is movably disposed at an outer end of the handle of an osteopathic intramedullary nail. The locating seat has one side which is parallel to the intramedullary nail and provided thereon with an adjustment device and an outer locating rod. The intramedullary nail and the outer locating rod can be kept relatively at precise position by means of the multi-sectional universal adjusting blocks for achieving an all-bearing adjustment and for drilling a locking screw hole rapidly.

7 Claims, 5 Drawing Sheets

7A
71A
71
18
71
18
61
7
52
7
41A'
5
3B'
51
32B'
34B'
35B
63
31B'
6
1
4A
41'
31A
3A
31A'
32A
3A'
35A
34A
41A
34A'
18A
18A
12
13A
11
15
13
2
34
34'
14
3
35
24
32
31
3'
33'
21
41
22

ALL POSITIONAL AND UNIVERSAL GUIDING DEVICE FOR INTERLOCKING INTRAMEDULLARY NAIL

BACKGROUND OF THE INVENTION

The present invention relates generally to an intramedullary nail guiding device, and more particularly to an all-bearing i.e., easily movable in any direction, and universal guiding device for an interlocking intramedullary nail.

The human skeleton is vulnerable to breakage upon being impacted by an external force. It is a general practice of osteopathy that a broken long bone of the lower extremities is fixed by an implanted intramedullary nail in conjunction with a locking screw.

Upon completion of implanting an intramedullary nail in a leg bone, it is necessary that a hole is drilled in the leg bone to receive the locking screw. However, such a drilling operation must be aided by an X-ray machine for locating the precise position of the hole of the intramedullary nail before the drilling operation is started. The entire preparatory process is rather tedious and time-consuming and is subject to an error caused accidentally by a loosened screw of the guiding device. In addition, the safety of a surgeon or a technician operating the X-ray machine can be jeopardized by an accidental leakage of X-rays.

SUMMARY OF THE INVENTION

It is, therefore, the primary objective of the present invention to provide an intramedullary nail with an all-bearing adjusting mechanism capable of cooperating with a corresponding guiding device drilling without the use of the X-ray machine for locating the precise position for the locking screw hole.

The structures, features and function of the present invention will be more readily understood by studying the following detailed description of the present invention in conjunction with the drawings provided herewith.

Figure 1:
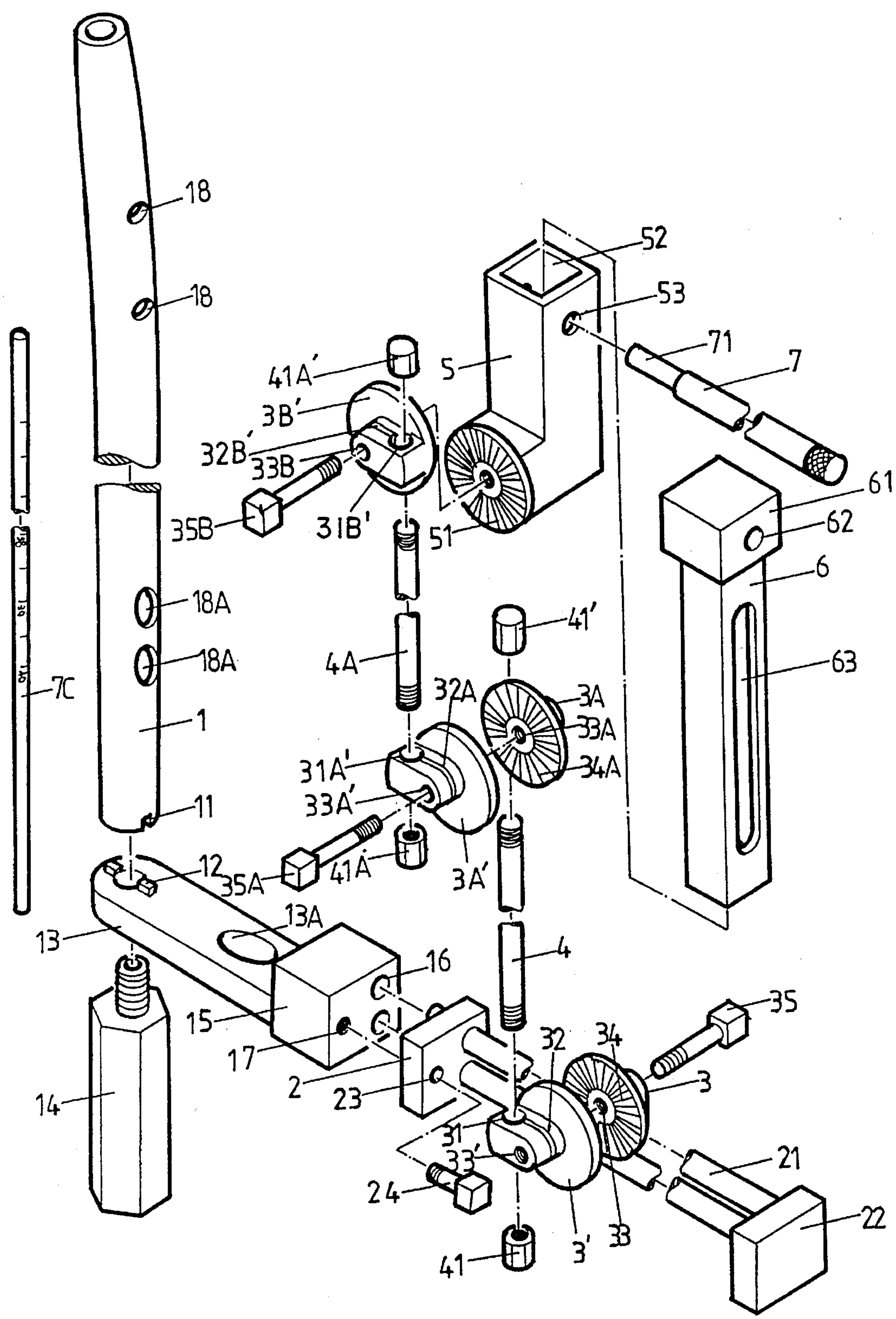
FIG. 1 shows an exploded view of the present invention.
Figures 2A, 2B:
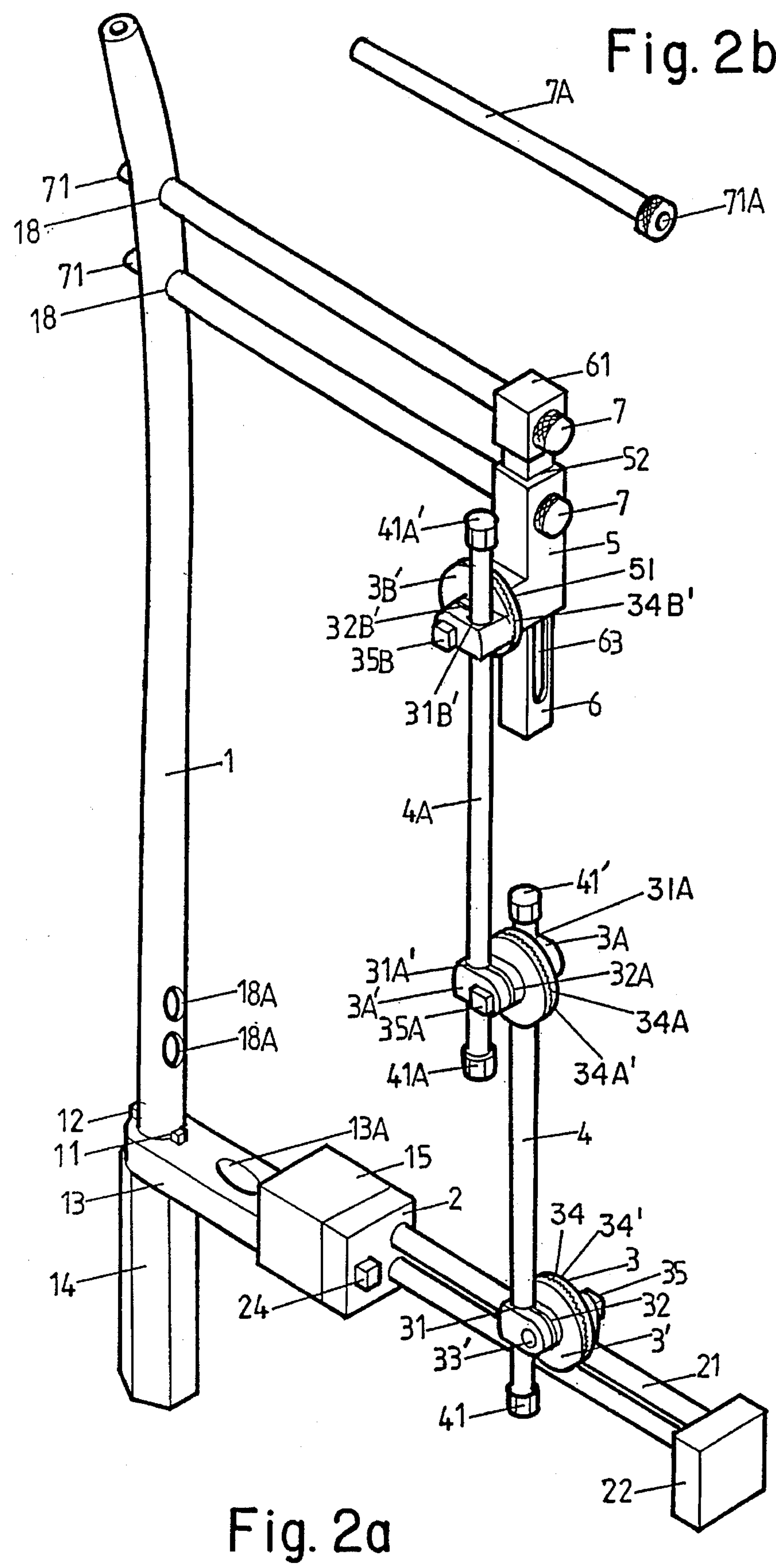
FIG. 2*a* shows a perspective view of the present invention in combination.
FIG. 2*b* shows a drill sleeve to be used with the present invention.

DETAILED DESCRIPTION OF THE INVENTION:

As shown in FIGS. 1 and 2*a*, an intramedullary nail 1 of the present invention is provided at the bottom thereof with a retaining slot 11 in cooperation with a retaining seat 13 having a protruded block 12. The retaining seat 13 is provided at the bottom thereof with a locking and tightening rod 14 engageable with the intramedullary nail 1. The retaining seat 13 is further provided with a connection seat 15 extending sidewards. The connection seat 15 is in turn provided with two guide holes 16 parallel to each other and with a threaded hole 17. The connection seat 15 has an outer end which is provided with a joining seat 2 attached thereto. The joining seat 2 is provided with two long guide rods 21 corresponding in location to the two guide holes 16. The two long guide rods 21 are provided respectively with an end block 22. The joining seat 2 is further provided at one end thereof with a fastening hole 23 in cooperation with a threaded nail 24 engageable with the threaded hole 17 of the connection seat 15. The guide rod 21 is provided with a universal adjusting block 3 which is in turn provided with a tightening hole 31 having in the side thereof a pressing slot 32 which is in turn provided with a locking hole 33 or a threaded area. The universal adjusting block 3 is further provided at another end thereof with a press thread cushion piece having regular press threads 34. The locking hole 33 of the universal adjusting block 3 is dimensioned to receive therein a threaded rod 35 engageable with a threaded hole 33' of another universal adjusting block 3' for uniting these two universal adjusting blocks. The universal adjusting block 3' has press threads 34'. A connection rod 4 is fitted into the tightening hole 31 of the universal adjusting block 3, with another end of the connection rod 4 being fitted into a tightening hole 31A of another universal adjusting block 3A, The connection rod 4 is provided at both ends thereof with end covers 41 and 41'. Another universal adjusting block 3A' having press threads 34A is provided with a tightening hole 31A' fitted with another connection rod 4A and end covers 41A and 41A'. Mounted on another end of the connection rod 4A is a universal adjusting block 3B' provided with tightening hole 31B' having in the side a pressing slot 32B' and further provided with a press thread cushion piece having press threads 34B'. Located at the end opposite to the press threads 34B' is a sleeve 5 provided with a press thread cushion piece having press threads 51 corresponding in location to the universal adjusting block 3B'. The universal adjusting block 3B' is further provided with a locking hole 33B to receive therein a threaded rod 35B engageable with a threaded hole in the sleeve 5. The sleeve 5 has a fitting hole 52 provided with a locating hole 53. The fitting hole 52 is dimensioned to receive therein a slide rod 6 which is provided at one end thereof with a locating seat 61 having a guide hole 62. The slide rod 6 is provided with an adjustment hole 63 of a slotted construction. The guide hole 62 and the locating hole 53 are provided therein respectively with a locating rod 7 extending to reach the locking screw connection hole 18 of the intramedullary nail 1.

Figure 3:
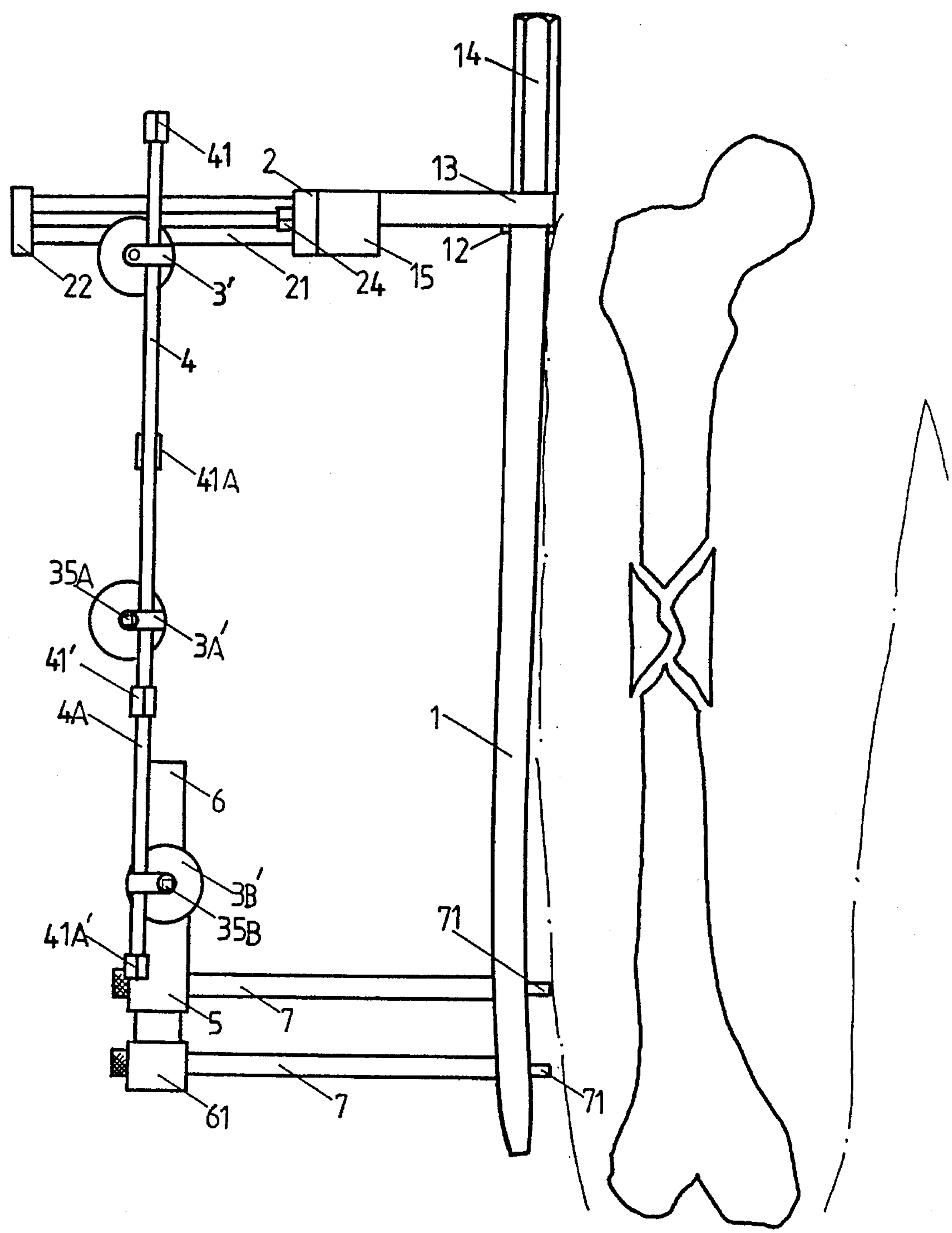
FIG. 3 shows a perspective schematic view of a connecting rod and a locating rod of the present invention in combination.
Figure 4:
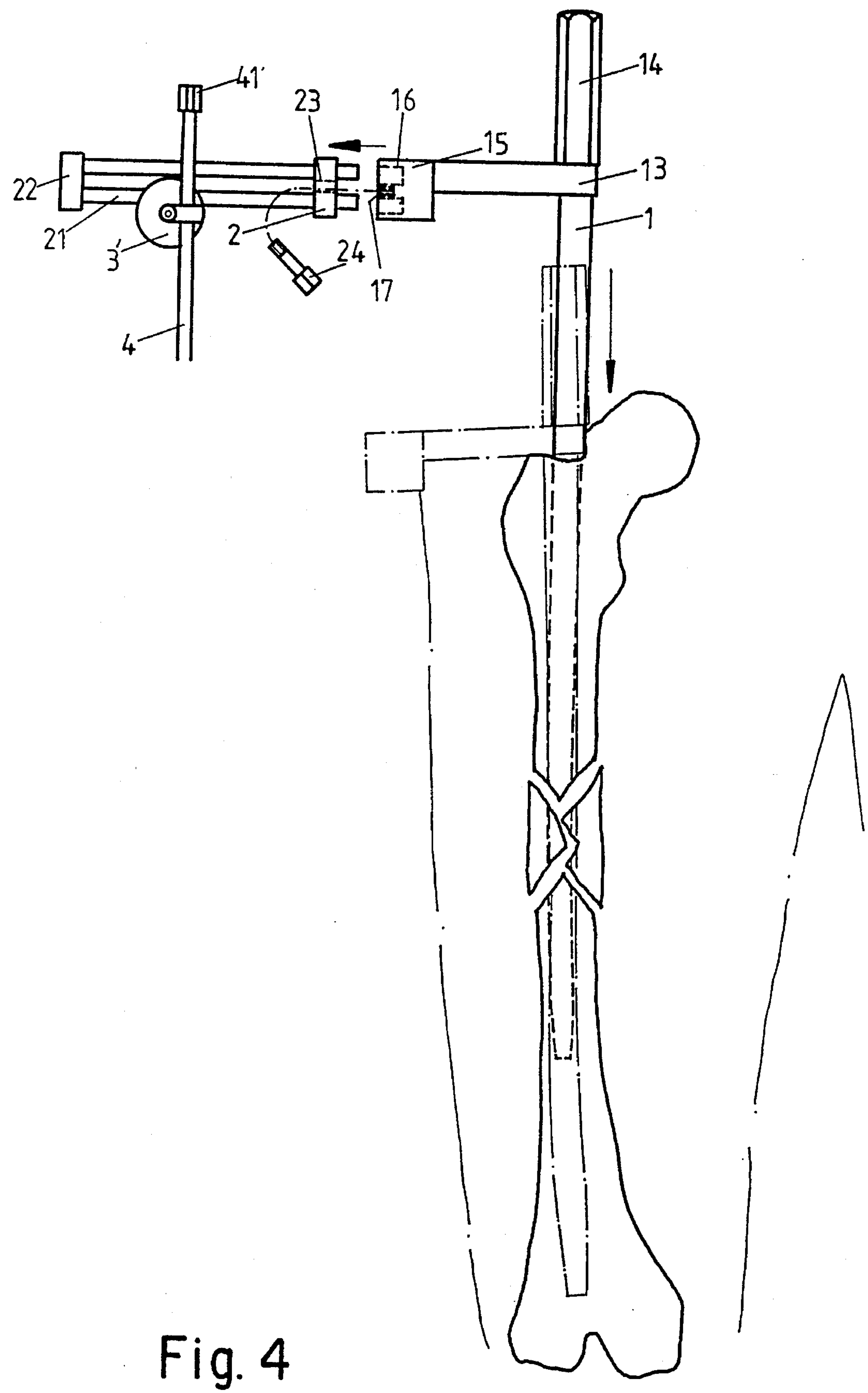
FIG. 4 shows a schematic view of an intramedullary nail being implanted into a medullar according to the present invention.
Figure 5:
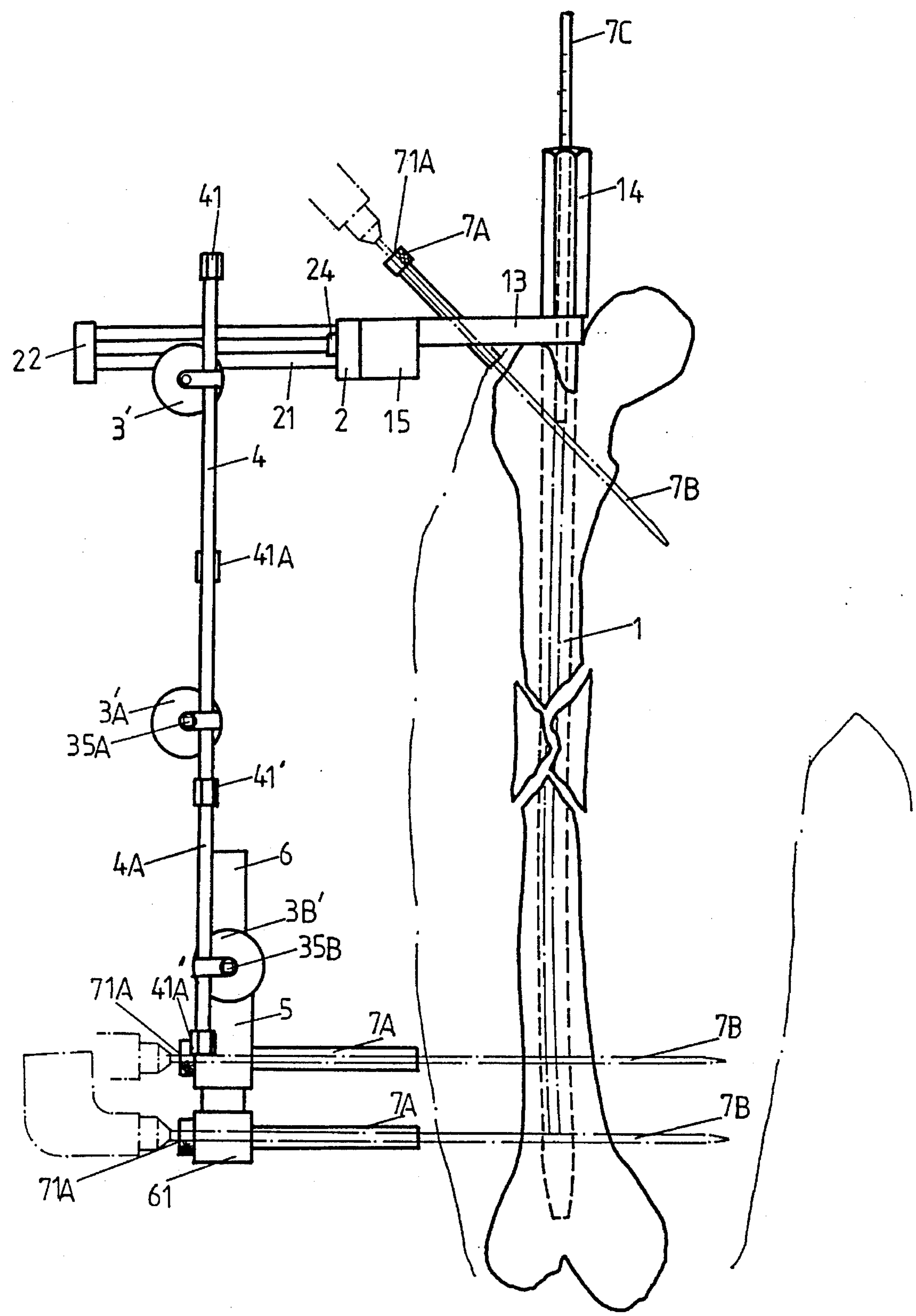
FIG. 5 shows a schematic view of the present invention at work.

As shown in FIGS. 3–5, the improved intramedullary nail 1 is provided at one end thereof with a connection seat 15 for mounting the universal adjusting blocks 3 and 3', which are slidably mounted on the guide rod 21. As a result, the distance between the universal adjusting blocks 3 and 3' can be slidably adjusted in accordance with the dimension of the leg of a person receiving the medical treatment. The locating hole 53 of the sleeve 5 and the guide hole 62 of the slide rod 6 are provided therein respectively with a locating rod 7 having at the front end thereof a locating shaft 71 engaging the threaded hole 18 of the intramedullary nail 1. The connection rods 4 and 4A are adjusted to be in opposite locations. The threaded rods 35,35A,35B of the universal adjusting blocks 3,3',3A,3A',3B' are tightened and locked respectively. The sleeve 5 and the slide rod 6 can be adjusted in an all-bearing manner in view of the fact that the connection rods 4 and 4A have a circular cross section and that the universal adjusting blocks 3, 3', 3A, 3A', 3B' and the sleeve 5 are provided respectively with the press thread cushions 34,34',34A,34A',34B' and 51. The locating hole 53 and the guide hole 62 are engageable with the threaded hole 18 of the intramedullary nail 1 which is made by any one of various manufacturers. The intramedullary nail 1 can be implanted to the medulla by drawing the locating rod 7 and loosening the threaded nail 24 of the joining seat 2 so as to separate everything from the nail 1 but the connection seat 15, the retaining seat 13 and the tightening rod 14. The nail 1 is then inserted in the bone. Upon reconnecting the joining seat 2 with the connection seat 15, the locating hole 53 and the guide hole 62 can be provided therein respectively with a drill sleeve 7A (about 1.8 m/m or 2 m/m). A drill pin 7B (about 1.8 m/m or 2.0 m/m K-pin) is put through the fitting hole 71A of the drill sleeve 7A to penetrate both ends of the leg bone. Before the drill pin 7B is drawn out, a graduated guide rod 7C is put into the inner hole of the intramedullary nail 1. The precise position of the drill hole can be determined by the sound produced by the contact of the guide rod 7C with the drill pin 7B inserted through holes 13A and 18A and by the unique scales marked on the guide rod 7C. The drill pin 7B is then drawn out and replaced by a guide sleeve 7A, shown in FIG. 2*b*, for drilling a larger hole (3.5–4.0 m/m), which is inspected to make sure it is all right before a locking screw is locked thereinto. Following the same procedures described above, another hole is drill at the second farther end and the end adjacent to the threaded hole 18A. The checking of the drill hole is done by the guide rod 7C which is graduated. The entire process is done without the use of the X-ray machine.

What is claimed is:

1. An all positional and universal guiding device for interlocking an intramedullary nail having a retaining slot orthogonal to a longitudinal axis of the nail, the guiding device comprising:

- a connection seat adapted to protrude from the retaining slot of the nail to be adjusted;
- a joining seat detachably connected to said connection seat;
- a first universal adjustable block;
- means for slidably mounting said first universal block to said joining seat;
- a connection rod inserted through said first universal adjustable block and extending parallel to the nail;
- a sleeve;
- a slide rod inserted into said sleeve and having a guide hole;
- a first locating rod inserted through said guide hole and outside said sleeve, said slide rod allowing the position of said first locating rod relative to the length of the nail to be adjusted; and
- a second universal adjustable block connecting said connection rod to said sleeve, said first and second universal adjustable blocks being adjustable along said connection rod.

2. The all positional and universal guiding device as recited in claim 1 wherein said sleeve further comprises a press thread cushion piece engaged with press threads of said second universal adjusting block, a threaded hole for securing said sleeve to said second universal block, and a fitting hole provided with a locating hole.

3. The all positional and universal guiding device of claim 2 wherein said slide rod is fitted into said fitting hole of said sleeve and provided at one end thereof with an adjusting slide slot and at another end thereof with a guide hole.

4. The all positional and universal guiding device of claim 2 further comprising a graduated guide rod for fitting into the nail to be adjusted, and wherein said first and second universal adjusting blocks are used to adjust an effective length of said connection rod and the angles of said sleeve and said graduated guide rod with respect to the nail to be adjusted so as to cause said locating hole and said guide hole to correspond in location to a respective connection hole of the nail to be adjusted.

5. The all positional and universal guiding device as recited in claim 1 wherein:

- said connection seat includes two guide holes and a first threaded hole;
- said slidably mounting means comprises two parallel guide rods, each having one end extending through and beyond said joining seat to said guide holes in said connection seat and another end provided with an end block, said another end of one of said two parallel guide rods being inserted through said first universal adjustable block;
- said joining seat includes a fastening hole; and
- said guiding device further comprises a threaded nail, inserted through said fastening hole and into said first threaded hole.

6. The all positional and universal guiding device as recited in claim 1 wherein said first universal adjusting block has press threads on one side and further comprises, on a side opposite said one side, a tightening hole receiving said connection rod, a pressing slot in the side of said tightening hole, and a second threaded hole through said universal adjusting block, said guiding device further comprising a press thread cushion piece having a locking hole and a threaded rod inserted through said locking hole and into said second threaded hole, said press threads of said universal adjusting block engaging with said press thread cushion device.

7. The all positional universal guiding device as recited in claim 1, wherein said sleeve includes a locating hole and said guiding device further comprises a second locating rod inserted through said slide rod and said locating hole of said sleeve, said first locating rod being adjustable relative to and independent of said second locating rod via said slide rod.

* * * * *